United States Patent
Kusunose et al.

(10) Patent No.: US 9,013,787 B2
(45) Date of Patent: Apr. 21, 2015

(54) MICROSCOPE AND INSPECTION APPARATUS

(71) Applicant: Lasertec Corporation, Yokohama-shi, Kanagawa (JP)

(72) Inventors: Haruhiko Kusunose, Yokohama (JP); Takamasa Tsubouchi, Yokohama (JP)

(73) Assignee: Lasertec Corporation, Kanagawa (JP)

( * ) Notice: Subject to any disclaimer, the term of this patent is extended or adjusted under 35 U.S.C. 154(b) by 245 days.

(21) Appl. No.: 13/744,890

(22) Filed: Jan. 18, 2013

(65) Prior Publication Data
US 2013/0188251 A1 Jul. 25, 2013

(30) Foreign Application Priority Data

Jan. 19, 2012 (JP) ................................ 2012-009233
Mar. 6, 2012 (JP) ................................ 2012-048949

(51) Int. Cl.
*G02B 21/06* (2006.01)
*G02B 21/00* (2006.01)
*G02B 21/10* (2006.01)
*F21V 8/00* (2006.01)
*G01N 21/95* (2006.01)

(52) U.S. Cl.
CPC ............ *G02B 21/06* (2013.01); *G02B 21/0092* (2013.01); *G02B 21/10* (2013.01); *G02B 6/0008* (2013.01); *G01N 21/9501* (2013.01)

(58) Field of Classification Search
CPC ....................................................... G02B 21/06
USPC ........................................ 359/386; 356/237.1
See application file for complete search history.

(56) References Cited

U.S. PATENT DOCUMENTS 5,887,009 A * 3/1999 Mandella et al. .................. 372/6
6,160,943 A * 12/2000 Davis et al. .................... 385/126

(Continued)

FOREIGN PATENT DOCUMENTS

JP 2006-178199 A 7/2006
JP 2009-282103 A 12/2009

(Continued)

OTHER PUBLICATIONS

JP Office Action with the relevant portion of the English translation issued on Jun. 12, 2012 in the counterpart Japanese application.

*Primary Examiner* — Frank Font
(74) *Attorney, Agent, or Firm* — Carrier Blackman & Associates, P.C.; William D. Blackman; Joseph P. Carrier

(57) ABSTRACT

A system including a microscope and an inspection apparatus in which an objective lens having a large numerical aperture is used for detecting a defect existing inside a sample. A light source apparatus produces linearly polarized light. The polarization maintaining fibers optically coupled to the light source apparatus project the linearly polarized light onto the sample surface as an illumination beam of P-polarized light at an incidence angle substantially equal to the Brewster's angle of the sample. The scattered light generated by the defect existing in the sample is emitted from the sample and is collected by the objective lens whose optical axis is perpendicular to the sample surface. Since the illumination beam of P-polarized light is projected at the incidence angle equal to the Brewster's angle of the sample, no surface reflection occurs and it is possible to use the objective lens having a large numerical aperture.

37 Claims, 9 Drawing Sheets

(56) References Cited

U.S. PATENT DOCUMENTS

2002/0030885 A1* 3/2002 Engelhardt et al. ........... 359/386
2012/0026311 A1* 2/2012 Ouchi et al. .................... 348/79

FOREIGN PATENT DOCUMENTS

| | | |
|---|---|---|
| JP | 2010-257585 A | 11/2010 |
| JP | 2011-102731 A | 5/2011 |

* cited by examiner

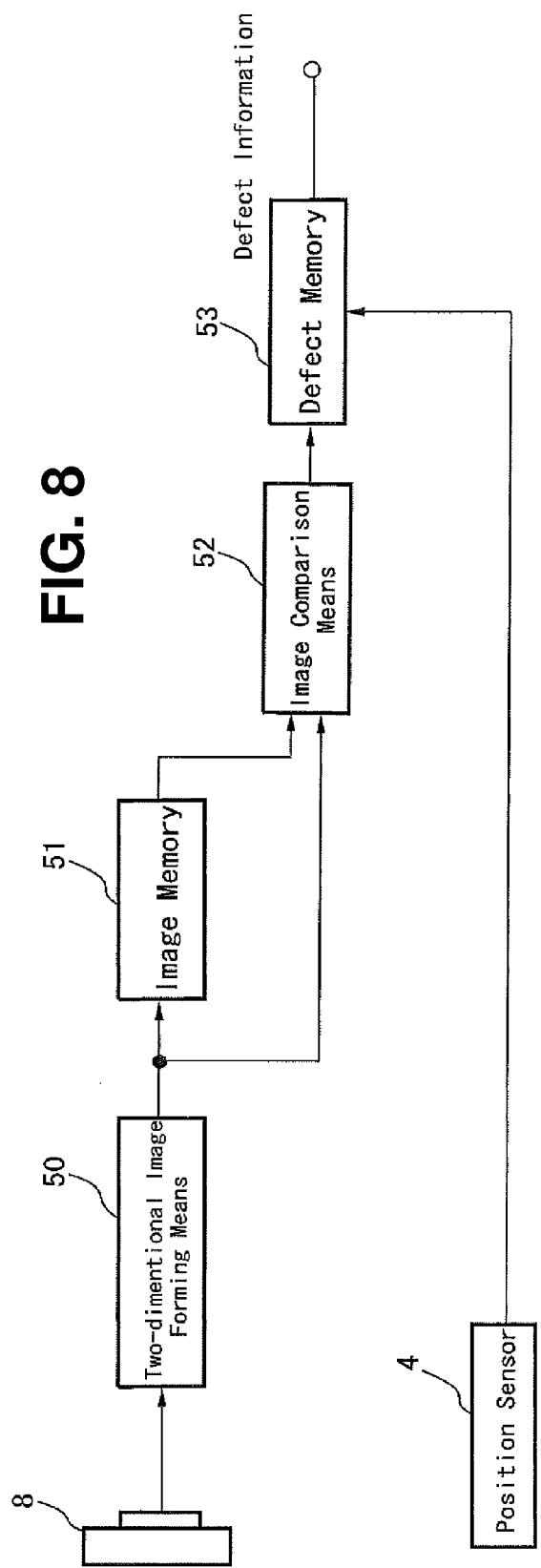

MICROSCOPE AND INSPECTION APPARATUS

TECHNICAL FIELD

The present invention relates to a microscope which is suitable to observe and inspect internal structures of various samples from outside of the sample.

The present invention also relates to an inspection apparatus which is suitable to detect a defect existing in a multilayered structure formed on a silicon substrate by use of darkfield illumination.

BACKGROUND ART

In a manufacturing process of a semiconductor device, various devices with a trench isolation have been developed. For example, as a MOSFET having high-voltage resistance, a MOSFET having a trench gate structure has been developed. Also, in the manufacturing process of an imaging device such as a CMOS sensor or a CCD sensor, the trenches are formed between the adjacent light receiving elements so as to prevent generation of crosstalk between the pixels. The depth of the trench influences the performance of the device and the yield rate of the production of the devices. For instance, in the production of the CMOS sensor, if the imperfect trench is formed, the leakage of the electric charges between the adjacent pixels may be increased, and the problem arises that the image quality is decreased.

A flash memory device with a laminate structure of memory elements has been developed. In the manufacturing process of the flash memory of the laminate type, a semiconductor layer and a silicon oxide layer are alternatively formed so as to form a multilayer structure. Then, in order to form a columnar transistor structure, a hole is formed in the multilayer structure and then a semiconductor material is embedded into the hole. In such manufacturing process of the flash memory device of the laminate type, if the hole to be formed in the multilayered structure is defective in structure owing to an etching process or if a foreign substance exists on the inner surface of the hole, the defective columnar transistor is formed and also the yield rate of the flash memory device is decreased. Therefore, the development of the microscope and inspection apparatus which can check whether the semiconductor layers are formed exactly or not and whether the various holes or grooves are correctly formed in the manufacturing step of the various semiconductor devices is strongly demanded. Furthermore, the development of the inspection apparatus which can detect the defective area existing in the multilayer structure including the hole and the groove from outside of the semiconductor body is strongly demanded.

In the manufacturing process of the semiconductor device, it has been known to observe or inspect the semiconductor substrate using the dark-field microscope (for example, see PLT 1). In this known dark-field microscope, since the sample surface is illuminated by use of an illumination beam having ring shape, the objective lens is arranged to form a dual structure, and an optical path of imaging optical system including the objective lens system is formed in the inside space and an optical path in which the illumination beam propagates is formed outside of the optical path of the objective lens system. The scattered light emanating from the sample surface is collected by the objective lens.

Further, a microscope in which the sample surface is illuminated by illumination beams having different wavelengths each other is also known (for example, see PLT 2). In this known microscope, a plurality of light sources for producing the illumination beams having different wavelengths are arranged outside of the optical path of the imaging optical system, and the illumination beams of different wavelengths are projected toward the illumination area including the optical axis of the objective lens. The wavelengths of the illumination beams are infrared region and visible region.

PLT 1: Japanese Patent Publication (A) No. 2006-178199
PLT 2: Japanese Patent Publication (A) No. 2010-257585

SUMMARY OF INVENTION

Technical Problem

As to the above mentioned dark-field microscope, since the lens barrel accommodating the objective lens system is arranged to be dual structure, the space for accommodating the objective lens is limited. By reason of this, the objective lens having large numerical aperture cannot be used, and thereby the defect detection of high resolution cannot be performed and also there is a limit in defect detection of high resolution. Furthermore, since strong surface reflection light is generated from the sample surface, the intensity of the flare is too much and there is a limit in the detection of the weak scattered light.

Furthermore, in the prior dark-field microscope, since the loss caused by the surface reflection is large, the quantity of the illumination light penetrating into the sample is smaller. Thereby, the intensity of the scattered light generated by the defect present in the hole and groove formed in the semiconductor layer is too weak, and thus the problem arises that the accuracy of the defect detection is decreased. Further, the prior dark-field microscope is aimed for the detection of the reflection light scattered by the sample surface and is not intended for the detection of the defect present in the internal structure of the sample.

An object of the present invention is to realize a microscope and an inspection apparatus in which the objective lens with large numerical aperture can be used in order to detect the defect existing in the sample with high resolution. Another object of the present invention is to realize a microscope and an inspection apparatus in which the surface reflection light is reduced and the illumination beam penetrating into the silicon body is increased.

Solution to Problem

The microscope according to the invention comprising a light source apparatus for producing linearly polarized light, a polarization maintaining fiber which is optically coupled to the light source apparatus to project the linearly polarized light emitted from the light source apparatus as an illumination beam of P-polarized light toward a sample surface, an objective lens which is arranged so that its optical axis is perpendicular to the sample surface so as to collect scattered light emitted from the sample, and a photo detector for receiving the scattered light collected by the objective lens, wherein said polarization maintaining fiber projects the illumination beam of the P-polarized light at an incidence angle which is substantially equal to the Brewster's angle of the sample.

According to the invention, the illumination beam of the P-polarized light is projected onto the sample surface at the incidence angle which is substantially equal to the Brewster's angle. As discussed below, when the illumination beam of the P-polarized light is projected onto the sample surface at the incident angle equal to the Brewster's angle, the surface reflectance of the sample surface becomes substantially equal to zero and the surface reflection light is not occurred. As a result, an illumination optical system in which most of the illumination light penetrates into the sample is obtained. Further, when the wavelength of the illumination light is about 800 nm, the Brewster's angle of silicon material is about 75°, and so the illumination beam is projected onto the sample surface at relatively large incident angle. As a result of this, since the spatial limitation for the objective lens is mitigated, it becomes possible to use the objective lens which has large numerical aperture and to carry out the defect inspection with high resolution. In addition, when the illumination beam is projected onto the sample surface at the incident angle equal to the Brewster's angle, the specular reflection light emanating from the sample surface is not collected by the objective lens, and thus it becomes possible to construct a dark-field illumination optical system. As a result, it is possible to detect the weak scattered light generated in the internal structure of the sample accurately. Furthermore, it becomes possible to carry out more accurate defect detection by use of the objective lens having large numerical aperture.

When a plurality of polarization maintaining fibers for projecting the illumination beam of the P-polarized light are provided and the light emitting ends of the polarization maintaining fibers are circularly arranged around the illumination area, the illumination area of the sample surface can be illuminated from different angular directions.

In a preferable embodiment of the microscope, the tip of the polarization maintaining fiber is provided with an optical element which controls the divergence angle of the illumination beam. When as the means for projecting the illumination beam, the polarization maintaining fiber is used, a diverging illumination beam emanates from the tip of the polarization maintaining fiber. Therefore, even if the optical axis of the polarization maintaining fiber is set at the Brewster's angle, the central portion of the illumination beam is made incident on the sample surface at the Brewster's angle but the marginal portion of the illumination beam is made incident at the incident angle which is slightly sifted from the Brewster's angle. For this reason, the problem arises that the surface reflection is occurred and the intensity of the illumination light penetrating into the sample is reduced. In order to solve such problem, according to the invention, the tip of the polarization maintaining fiber is provided with an optical element which controls the divergence angle of the illumination beam. If the diverging angle of the illumination beam is controlled, amount of the beam portion which is projected at the incident angle shifted from the Brewster's angle is reduced and it becomes possible to reduce the surface reflection. In particular, if an optical element (a lens element) which functions as a collimator lens is used, the parallel illumination beam in parallel with the optical axis of the polarization maintaining fiber is emitted from the polarization maintaining fiber, and thus the whole of the illumination beam of P-polarized light is made incident upon the sample surface at the Brewster's angle. As a result, it is possible to construct an illumination system in which no surface reflection is occurred and most of the illumination light penetrates into the sample. Furthermore, as specific advantageous effect, since the parallel illumination beam in parallel with the optical axis is projected onto the sample surface, an illumination having uniform brightness distribution. As the lens element, a gradient index lens or a rod lens in which its end face is formed as a spherical surface can be used.

In another preferable embodiment of the microscope, the light source apparatus comprises a plurality of super luminescent light emission diodes (SLED or SLD) which function as a point light source and produce an incoherent light beam of the linearly polarized light, and the polarization maintaining fiber is coupled to the super luminescent light emission diodes through a plurality of optical fiber couplers. The inventor analyzed the super luminescent light emission diode and as a result learned that the super luminescent light emission diode has specific characteristics different from a laser source and a LED. Firstly, the super luminescent light emission diode produces the light beam of the linearly polarized light. Secondly, the super luminescent light emission diode functions as a point light source unlike an LED. And thirdly, the super luminescent light emission diode produces an incoherent light beam unlike a laser.

The SLED produces the illumination beam of the linearly polarized light. Therefore, if the polarization maintaining fiber is coupled to the SLED, it can make the light beam emitted from the SLED propagate to the illumination area of the sample surface with maintaining its polarization state. As a result of this, it becomes possible to project the illumination beam of the P-polarized light onto the sample surface only by arranging the polarization maintaining fiber suitably. Here, the P-polarized light means the light in which the electric vector oscillates in parallel with the plane of incidence. And, the plane of incidence means a plane which includes the optical axis of the illumination beams and is perpendicular to the sample surface.

The polarization maintaining fiber is a single mode optical fiber. In order to make the illumination beam penetrate into the single mode optical fiber efficiently, it is necessary that the light source acts as a point light source. In this case, since the SLED acts as the point light source, if the SLED is used as the illumination light source, it is possible to make the illumination light emitted from the SLED penatrate into the single mode optical fiber efficiently. On the contrary, since a normal light emission diode (LED) acts as a plane emission light source, when the LED is connected to the polarization maintaining fiber, the problem arises that the optical connection loss is increased.

It is necessary that the illumination beam emitted from the polarization maintaining fiber forms an illumination area having uniform brightness distribution on the sample surface. As the incoherent light beam without speckle patterns can be produced from the SLED, the illumination area having uniform brightness distribution can formed on the sample surface. On the contrary, a laser source produces the laser beam consisting of the linearly polarized light, but it generates a coherent light beam and thereby emitted laser beam includes a number of speckle patterns. Therefore, when the laser source is used as the illumination source, it is extremely difficult to form the illumination area having uniform brightness distribution on the sample surface. On the basis of the above explained characteristics of the SLED, it is preferable to use the super luminescent light emission diode (SLED or SLD) as the illumination source.

In another preferable embodiment of the microscope according to the invention, the light source apparatus comprises a plurality of super luminescent light emission diodes for producing the light beams having different wavelengths each other so as to illuminate the illumination area formed on the sample surface using the illumination beams having different wavelengths by selectively turning on the super luminescent light emission diodes. As explained above, since the SLED acts as the point light source, it can be couple to the polarization maintaining fibers efficiently. In addition, it is possible to connect a 3 dB coupler or a WDM coupler (Wavelength Division Multiplexing) to the polarization maintaining fiber. Therefore, when a plurality of SLEDs for producing the light beams having different wavelengths each other are prepared and these SLEDs are coupled to the polarization maintaining fiber used to project the illumination beam through the 3 dB coupler and WDM coupler as well as the polarization maintaining fibers used for connection, it becomes possible to selectively project the illumination light having the desired wavelength only by switching the driving current which is supplied to the SLEDs. As a result, it becomes possible to illuminate the sample by use of the illumination beam having an optimum wavelength depending on the optical characteristics of the sample to be viewed or inspected.

The microscope according to the invention comprises a light source apparatus including one or a plurality of super luminescent light emission diodes which produce an incoherent light beam of linearly polarized light, one or a plurality of polarization maintaining fibers which are optically coupled to the light source apparatus to project the linearly polarized light emitted from the light source apparatus onto a sample surface as illumination beams of P-polarized light, an objective lens which is arranged so that its optical axis is perpendicular to the sample surface so as to concentrate the scattered light emitted from the sample, and a photo detector for receiving the light collected by the objective lens, wherein each tip of the polarization maintaining fibers is provided with an optical element which functions as a collimator lens, and wherein the polarization maintaining fibers project the illumination beams of the P-polarized light at an incidence angle which is substantially equal to the Brewster's angle onto the sample surface.

In the microscope of the invention, since the SLED is used as the illumination source and the tip of the polarization maintaining fiber is provided with the optical element which functions as the collimator lens, the whole of the illumination beam is projected onto the sample surface at an incidence angle which is substantially equal to the Brewster's angle. Further, the SLED produces the light beam having uniform brightness distribution, the illumination area having the uniform brightness distribution on the sample surface. As a result of this, the whole of the illumination beam penetrates into the sample, and thereby the dark-field illumination system is constructed.

In the preferable embodiment of the microscope, the sample is a semiconductor body comprising a silicon substrate and one or a plurality of semiconductor layers formed on the silicon substrate, the super luminescent light emission diode produces the illumination beam of infrared light which is transparent to the silicon material, and the objective lens collects the scattered light generated inside of the semiconductor layers or the scattered light generated by a hole or a groove formed in the semiconductor layer. If the SLED for producing the infrared light which is transparent to the silicon material is used as the illumination source, the illumination beam projected at the incident angle equal to the Brewster's angle penetrates into the silicon material layer and the silicon substrate. And also, the scattered light generated in the silicon material layer transmits through the silicon layer and the silicon substrate, and thus the microscope and the inspection apparatus suitable for detecting the defect existing in the semiconductor layer is constructed.

The inspection apparatus of the invention comprises a stage arranged to move along a first direction and a second direction perpendicular to the first direction and to hold a sample to be inspected, a light source apparatus for producing linearly polarized light, a polarization maintaining fiber which is optically coupled to the light source apparatus to project the linearly polarized light emitted from the light source apparatus as an illumination beam of P-polarized light toward a sample surface, an objective lens which is arranged so that its optical axis is perpendicular to the sample surface so as to collect scattered light emitted from the sample, a photo detector for receiving the scattered light collected by the objective lens, and a signal processing unit coupled to the photo detector and processing the output signals supplied from the photo detector to produce data indicative of the defect, wherein said polarization maintaining fiber projects the illumination beam of the P polarized light at an incidence angle which is substantially equal to the Brewster's angle of the sample.

According to the inspection apparatus of the invention, since the light source apparatus including one or a plurality of SLEDs for producing the light beam of the linearly polarized light is used, the illumination area having uniform brightness distribution can be formed on the sample surface. That is, when a laser source is used as the illumination source, it is difficult to form the illumination area having the uniform brightness distribution, because the laser beam includes a large number of speckle patterns.

In a preferred embodiment of the inspection apparatus, the tip of the polarization maintaining fiber is provided with an optical element which controls the divergence angle of the illumination beam. When only the polarization maintaining fiber is used as the means for projecting the illumination beam toward the sample surface, the divergent illumination beam is projected onto the sample surface and thus the problem arises that the brightness of the marginal portion of the illumination area is decreased. And also, the marginal beam portion of the illumination beam is made incident on the sample surface at the incident angle displaced from the Brewster's angle. On the contrary, according to the invention, since the diverging beam is converted into the parallel illumination beam by the optical element and the parallel illumination beam is projected onto the sample surface, the whole of the illumination beam is made incident on the sample surface at the incident angle equal to the Brewster's angle. Thereby, an illumination optical system in which substantially no surface reflection occurs is constructed.

An inspection apparatus of the invention for detecting a defect existing in a semiconductor body having a silicon substrate and a multilayer structure formed on the substrate comprises a stage arranged to move along a first direction and a second direction perpendicular to the first direction and to support the semiconductor body to be inspected, a light source apparatus including one or a plurality of super luminescent light emission diodes for producing light beams of linearly polarized light having a wavelength of infrared region, one or a plurality of polarization maintaining fibers which are optically coupled to the light source apparatus to project the light beam of the linearly polarized light emitted from the light source apparatus as an illumination beam of P-polarized light toward the semiconductor body, an objective lens which is arranged so that its optical axis is perpendicular to the semiconductor body arranged on the stage so as to concentrate the scattered light emitted from the semiconductor body, a photo detector for receiving the scattered light collected by the objective lens, and a signal processing unit coupled to the photo detector and processing the output signals supplied from the photo detector to produce data indicative of the defect, wherein the tip of the polarization maintaining fiber is provided with an optical element which functions as a collimator leans, and wherein said polarization maintaining fiber projects the illumination beam of the P-polarized light at an incidence angle which is substantially equal to the Brewster's angle of the semiconductor body.

As explained above, the Brewster's angle of the silicon at the wavelength of the infrared region is about 75°, and thus the illumination beam is projected onto the sample surface at relatively large incident angle. As a result, since the limitation for the objective lens is mitigated, it is possible to use an objective lens having a large numerical aperture and to carry out more accurate defect inspection. In addition, since the dark-field illumination system is constructed, it becomes possible to detect the scattered light generated in the silicon body accurately, even if the intensity of the scattered light is weaker. That is, the synergy effect of using the dark-field illumination system and the objective lens having the large numerical aperture is achieved, and so can carry out more accurate defect inspection. Moreover, since the whole of the illumination beam is projected onto the sample surface at the Brewster's angle, the advantageous effect is achieved that no surface reflection does occurs and the illumination area having uniform brightness distribution is formed on the sample surface.

In the manufacturing process of a CMOS sensor and CCD sensor, various semiconductor layers are formed on the silicon substrate, and thereafter the rear surface of the silicon substrate is polished. In such manufacturing process, if the defects formed inside of the silicon body can be detected during the process, it will be possible to increase the yield rate of the semiconductor devices. According to the invention, the silicon body is scanned using the illumination beam of the infrared light which is transparent to the silicon material. Therefore, the scattered light generated in the silicon body is emitted from the rear surface of the silicon substrate, and thus the scattered light can be collected by the objective lens. Moreover, according the invention, since the dark-field illumination is carried out and the objective lens having the large numerical aperture can be used, it becomes possible to perform more accurate defect inspection.

In a preferred embodiment of the inspection apparatus, the illumination beam is projected onto the rear surface of the silicon substrate which is not provided with the multi-layer structure, and the objective lens captures the scattered light generated in the multi-layer structure and emitted from the rear surface of the silicon substrate. Advantageous Effect of Invention According to the invention, since the illumination beam of the P-polarized light is projected toward the sample surface at the incidence angle which is substantially equal to the Brewster's angle, most of the illumination light can penetrates into the sample. As a result of this, it become possible to use the objective lens having a large numerical aperture and to construct the dark-field illumination system in which the flare light is substantially reduced, and thus it become possible to detect the defect existing in the sample more accurately.

Furthermore, since the super luminescent light emission diode (SLED) functions as a point light source and produces the incoherent and linearly polarized light including no speckle pattern, it is possible to form the illumination area having uniform brightness distribution on the sample surface.

Furthermore, if the tip of the polarization maintaining fiber is provided with the optical element which functions as the collimator lens, the parallel illumination beam emanates from the optical element, and thus the whole of the illumination beam can be made incident on the sample surface at the incident angle which is substantially equal to the Brewster's angle. Therefore, most of the illumination beam penetrates into the sample and the illumination area having the uniform brightness distribution can be formed.

BRIEF DESCRIPTION OF DRAWINGS

[FIG. 8] is a view showing one example of a signal processing unit.

EMBODIMENTS OF INVENTION

Figure 1:
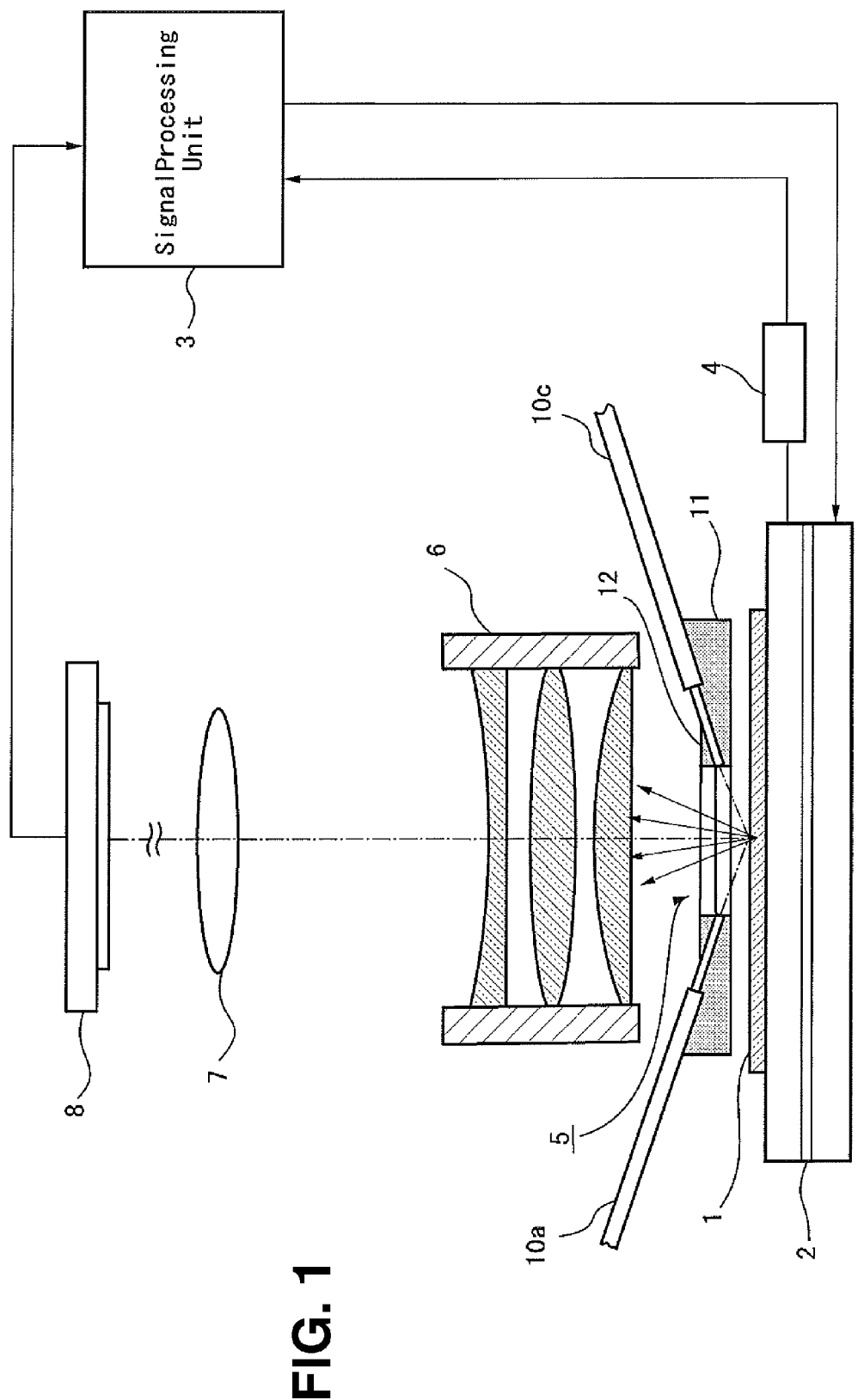
[FIG. 1] is a view showing an overall structure of the inspection apparatus comprising the microscope of the present invention.
Figure 2:
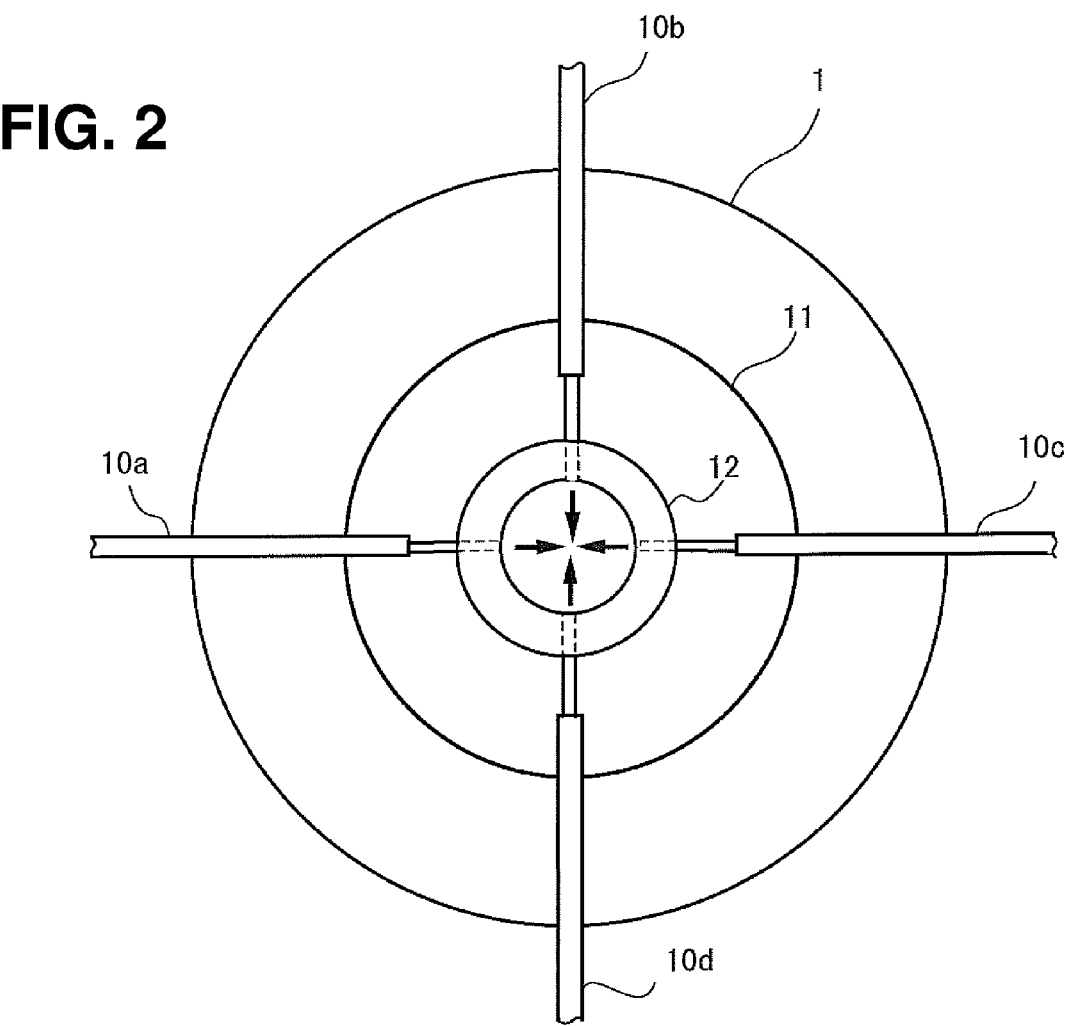
[FIG. 2] is a plan view showing one example of an illumination beam projecting section.
Figure 3:
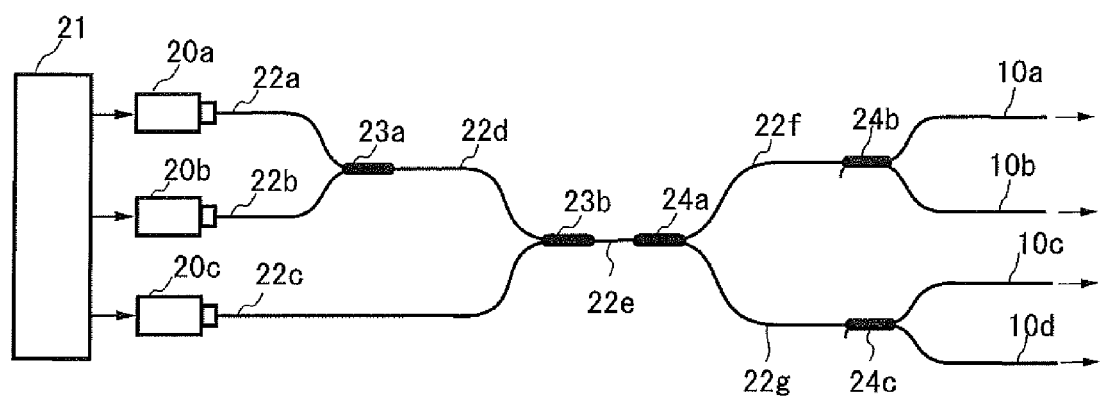
[FIG. 3] is a view showing one example of a light source apparatus which is used for the microscope and inspection apparatus according to the invention.

FIG. 1 is a view showing an overall structure of the inspection apparatus comprising the microscope of the present invention. FIG. 2 is a plan view showing an illumination beam projecting section of the inspection apparatus shown in FIG. 1 and FIG. 3 is a view showing one example of a light source apparatus. According to the invention, the defect detection is carried out by performing dark-field illumination to a sample surface and by detecting scattered light generated in the sample. The sample 1 (semiconductor body) to be inspected is arranged on the stage 2. In the present example, as the substrate to be inspected a semiconductor body comprising a semiconductor substrate and a multilayered structure formed on the substrate is used, and various defects such as a defect formed in the multilayered structure and a defect existing in a wiring pattern are detected. As the semiconductor body, for example a silicon body comprising a silicon substrate and the multilayered structure composed of silicon material layers and silicon oxide layers is used.

As to the stage 2, X-Y stage which is movable in a first direction (X direction) and a second direction (Y direction) perpendicular to the first direction is used. The stage 2 holds the sample and performs a scanning operation. The stage 2 moves in the X and Y directions in a zigzag fashion by use of driving signals supplied from signal processing unit 3, and thereby the whole surface of the semiconductor body is scanned by the illumination beam. A position sensor 4 is connected to the stage 2, and the position of the stage 2 in the X and Y directions during movement is detected. The detected position information of the stage 2 is supplied to the signal processing unit 3. The signal processing unit 3 specifies the address of the detected defect using the supplied position information of the stage.

In the illumination beam projecting section 5, the illumination beam projecting fibers 10a and 10b which are composed of the polarization maintaining fiber project the illumination beam of optically transparent illumination light is projected toward the semiconductor body 1 arranged on the stage. As shown in FIG. 1, the illumination beam projecting section 5 comprises four illumination beam projecting fibers 10a~10d, but only two illumination beam projection fibers 10a and 10c are shown in FIG. 1. When the illumination beam is projected from the illumination beam projecting fiber, an illumination area is formed on the surface of the semiconductor body 1. The illumination beam projecting fiber projects the illumination beam of P-polarized light at an incidence angle which is substantially equal to the Brewster's angle toward the surface of the semiconductor body. Therefore, as explained below, the reflectivity at the surface of the semiconductor body 1 becomes substantially zero and most of the illumination light penetrates into the semiconductor body. When the defect exists in the semiconductor body, the scattered light is generated by the defect. The scattered light is emitted from the semiconductor body and is collected by an objective lens 6. The covering of the tip portion of the illumination beam projecting fiber is removed so as to expose the cladding of the fiber.

The scattered light collected by the objective lens 6 is made incident on photo detector means 8 through an imaging lens 7. As the photo detector means, a TDI sensor is used. The charge transferring speed of the TDI sensor is set to correspond to the main scanning speed of the stage 2. The image signal outputted from the TDI sensor is supplied to the signal processing unit 3. Alternatively, a two dimensional CCD sensor can be used as the photo detector means.

The signal processing unit 3 forms a dark-field image using the scattered light emitted from the semiconductor body. Then, the signal processing unit detects the defect by performing the die to die comparison checking or the die to database comparison checking using the dark-field image, and specifies the address of the detected defect. If a foreign substance is present in the hole or groove formed in the semiconductor layer or the multilayered structure, such foreign substance forms the defect. That is, when the illumination light strikes on the foreign substance or the defect, the illumination light is scattered by the foreign substance and the scattered light is generated from the foreign substance. Then, the scattered light generated from the defect is collected by the objective lens. Therefore, the defect can be detected by performing the die to die comparison checking using the dark-field image. Further, fine evenness may be formed on the bottom surface of the contact hole or trench when the etching process is carried out. In this case, when the illumination light strikes on the bottom surface of the contact hole or trench, the scattered light is generated from the bottom surface. Therefore, if the hole or trench having predetermined depth is not formed in the semiconductor layer due to imperfect etching, the image of the scattered light is formed at the deviated position from the correct position. Therefore, it is possible to detect the imperfect hole or trench by the die to die comparison checking or die to database checking using the dark-field image. Moreover, in the manufacturing process using TSV technique, the correct TSV is not formed in the semiconductor body due to the incomplete etching, the defective portion can be detected by detecting the scattered light generated in the semiconductor body. Furthermore, although the scattered light is also generated from the normal portion, such scattered light is cancelled in the die to die comparison checking process, and thus it is possible to detect only the scattered light generated from the defective portion.

Next, the illumination beam projecting method will be explained. FIG. 2 is a plan view showing the illumination beam projecting section 5 viewed along the optical axis of the objective lens. The illumination beam projecting section 5 comprises four illumination beam projecting fibers (polarization maintaining fibers) 10a~10d for projecting the illumination beam onto the surface of the semiconductor body 1, a supporting plate 11 for supporting the illumination beam projecting fibers, and a pressing plate 12 for fixing the illumination beam projecting fibers to the supporting plate. Each cover of the tip portions of four illumination beam projecting fibers 10a~10d is removed. Four V-shaped grooves are circularly formed around the illumination area at the surface of the supporting plate. Four polarization maintaining fibers are placed in the groove, respectively and are fixed using adhesive. Further, the pressing plate is attached to the supporting plate using the adhesive. In the present example, the illumination beam projecting section comprises four illumination beam projecting fibers are used, but it is possible to use only one polarization maintaining fiber and to scan the sample surface by one illumination beam.

Each V-shaped groove formed at the supporting plate is inclined so that the illumination beam is made incident on the sample surface at the incident angle which is substantially equal to the Brewster's angle of the sample. For instance, when the inside of the semiconductor layer or multilayered structure formed on the silicon substrate is inspected using the near infrared light, the Brewster's angle of the silicon material is about 75°. Therefore, the polarization maintaining fibers 10a~10d are supported so that the illumination beams emanating from the polarization maintaining fibers are made incident on the surface of the semiconductor body at the incident angle which is equal to 75°. Since each Brewster's angle of the samples is different each other due to the optical characteristic of the samples, it is preferable to prepare the supporting plate corresponding to the optical characteristic of the sample. Furthermore, it is preferable that the incident angle of the illumination beam corresponds to the Brewster's angle of the sample strictly, but the incident angle of the illumination beam may be set to slightly deviate from the Brewster's angle of the sample. That is, even if the incident angle of the illumination beam slightly deviates from the Brewster's angle of the sample, the similar effect can be achieved.

Further, in the present example, four polarization maintaining fibers are circularly arranged about the illumination area at equal angle. Thereby, the illumination area of the sample surface is illuminated from different angular directions.

According to the invention, the light source apparatus produces the light beam of linearly polarized light, and the light beam is projected onto the surface of the semiconductor body through the polarization maintaining fiber which is optically coupled to the light source apparatus as the illumination beam of the P-polarized light. Therefore, the polarization maintaining fibers 10a~10d are set so that the illumination light emitted from the light source apparatus is made incident on the surface of the semiconductor body 1 as the P-polarized light. That is, each polarization maintaining fiber is configured in such a manner that the oscillation direction of the electric vector of the illumination light emitted from the light source apparatus is parallel to the incident plane.

Next, the light source apparatus will be explained. In the present example, the light source apparatus comprises three super luminescent light emission diodes 20a~20c which produce the light beams having different wavelengths each other, and the illumination beam of optimum wavelength region is projected based on the optical characteristics of the sample. For example, when the inspection is carried out for the semiconductor body having the multilayered structure, the multilayered structure may operate as an interferential layer. In this case, reflection light reflected by an interface between semiconductor layers may be increased and the intensity of the illumination light passing through the multilayered structure may be decreased. In such case, the intensity of the reflected light may be decreased by suitably selecting the wavelength of the illumination light based on the thickness or the refractive index of the semiconductor layer.

In the present example, the first SLED 20a produces the illumination light having a center wavelength λ1 of 680 nm, the second SLED 20b produces the illumination light having a center wavelength λ2 of 1310 nm, and the third SLED 20c produces the illumination light having a center wavelength λ3 of 1550 nm. These SLEDs 20a~20c are connected to a control circuit 21 and are selectively turned on or turned off by switching the driving current which is supplied to the SLEDs 20a~20c. Further, the above-mentioned wavelengths of the illumination light are one example, and it is possible to select the SLED which produces the illumination light having optimum wavelength based on the characteristic of the sample.

The SLED has a specific feature to produce a light beam of linearly polarized light and to operate as a point light source. Therefore, since the SLED operates as a point light source, when a single mode optical fiber is optically connected to the SLED, it is possible that most of the light beam emitted from the SLED can penetrate into the single mode optical fiber without connection loss. On the contrary, a typical light emission diode (LED) is a surface light-emitting device. Therefore, when the single mode optical fiber is connected to the LED, the problem arises that the significant connection loss occurs. Furthermore, the SLED produces the light beam of the linearly polarized light. Therefore, if a polarization maintaining fiber is connected to the SLED, it is possible that the light beam emitted from the SLED can propagate to the sample surface in the condition where its polarization state is maintained. Thereby, by configuring the polarization maintaining fiber suitably, the illumination beam of the P-polarized light can be projected onto the sample surface. As explained below, if the illumination beam of the P-polarized light is projected onto the sample surface at the incident angle which is equal to the Brewster's angle of the sample, the reflectivity of the sample surface becomes zero and thus no surface reflection occurs. As a result of this, an illumination system in which the flare is substantially reduced and the efficient use of the illumination beam is significantly improved can be realized. Moreover, the SLED produces a light beam which has a relatively broad spectrum and is incoherent, and thus the illumination beam without speckle pattern can be projected. In consideration of the advantageous effect of the SLED, in the present example, the SLED (super luminescent light emission diode) is used as the illumination source.

The first~third polarization maintaining fibers 22a~22c are connected to the SLEDs 20a~20c, respectively. The first and second polarization maintaining fibers 22a and 22b are connected to a first WDM coupler (Wavelength Division Multiplexing coupler) 23a. The light exiting end of the first WDM coupler is connected to a forth polarization maintaining fiber 22d. The forth polarization maintaining fiber 22d and the third polarization maintaining fiber 22c are connected to a second WDM coupler 23b, the light exiting end of which is connected to a fifth polarization maintaining fiber 22e. The light exiting end of the fifth polarization maintaining fiber 22e is connected to a first 3 dB coupler 24a. A sixth and seventh polarization maintaining fibers 22f and 22g are connected to the light exiting end of the first 3 dB coupler 24a. The sixth polarization maintaining fiber 22f is connected to a second 3 dB coupler 24b. The first and second illumination beam projecting fibers 10a and 10b are connected to the light exiting end of the second 3 dB coupler 24b. The third and forth illumination beam projecting fibers 10c and 10d are connected to the seventh polarization maintaining 22g through a third 3 dB coupler 24c.

When the driving current is supplied to either of the first~third SLEDs 20a~20c under the controlling of the control circuit 21 to produce the light beam, the light beam emitted from the SLED is made incident on the illumination beam projecting fibers 10a~10d uniformly. Then, the illumination beams having uniform intensity are emitted from the illumination beam projecting fibers 10a~10d in the condition where the polarization states are maintained. In this way, the wavelength of the illumination light can be selected, and thus the sample can be illuminated by the illumination light having the optimum wavelength based on the sample characteristic. For instance, when the semiconductor body to be inspected is a semiconductor multilayered structure, the optimum illumination condition can be set one by one in consideration of the thickness or refractive index of the semiconductor layer of the sample.

As alternative embodiments of the light source apparatus shown in FIG. 3, the following operation aspects can be applied. Firstly, upon start of the inspection, all of three SLEDs 20a~20c are turned on at the same time. In this case, since the illumination beams including three light beams having different wavelength each other are made incident on the illumination projecting fibers 10a~10d, the sample surface is simultaneously scanned by three light beams having different wavelength each other. In this case, the sample surface is simultaneously scanned by the plural illumination beams having different wavelength each other, and thus it is possible to generate the scattered light and to detect the defective portion, even if there is local portions having high reflectivity or high refractive index for a specific wavelength in the sample.

Furthermore, it is possible that the three SLEDs 20a~20c respectively produce the light beam having the same wavelength and are turned on at the same time. In this case, since the light beams emitted from three SLEDs are emitted from the four illumination projecting fibers 10a~10d uniformly, each illumination projecting fiber can project the illumination beam having the intensity of three times in comparison with the case of turning on only one SLED. Therefore, such embodiment is advantageous for the case where the intensity of the light beam emitted from the SLED is not sufficient.

In the above-mentioned embodiment, the light source including three SLEDs was used as the light source apparatus, but it is possible to use a light source apparatus including one SLED. Further, a combination of one SLED and one polarization maintaining fiber can be used. In this case, it is possible to connect a polarization maintaining fiber which operates as the illumination beam projecting fiber to the SLED directly.

Figure 4:
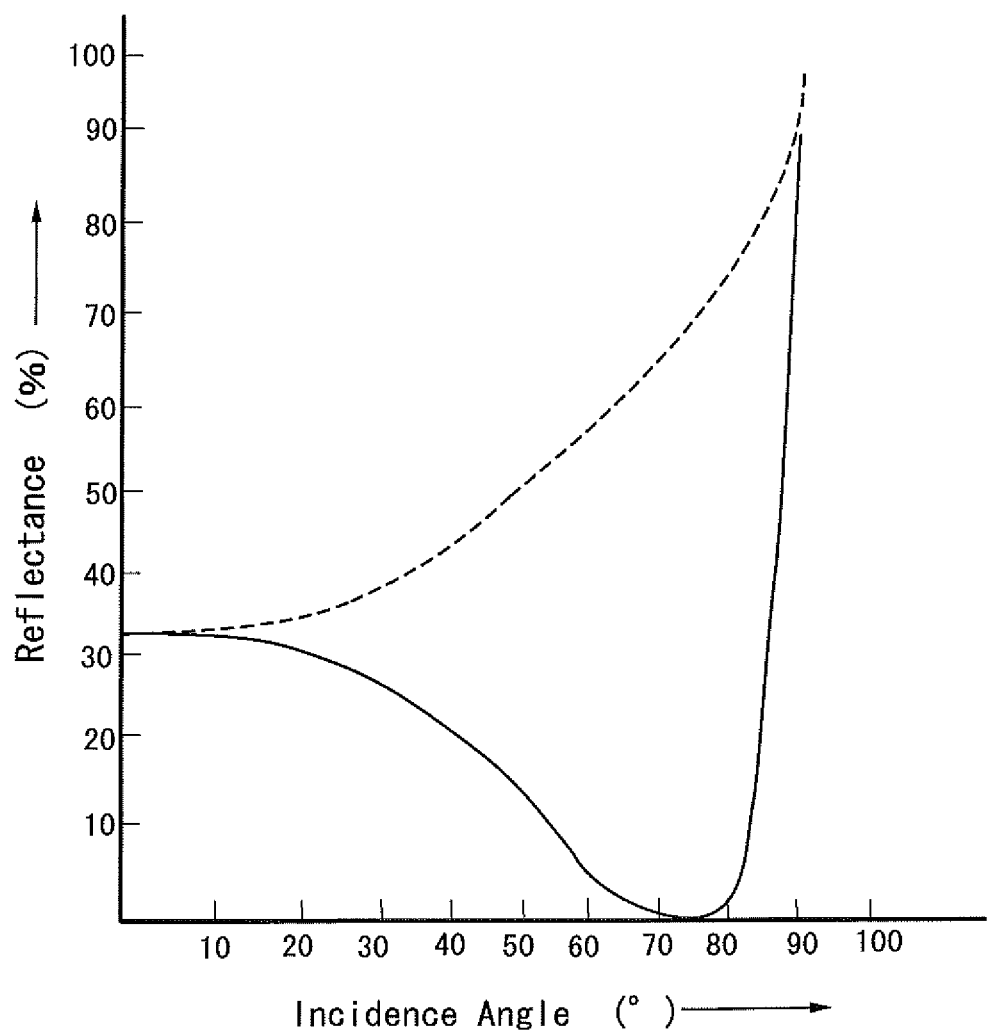
[FIG. 4] is a graph showing relation between incident angle and reflection index of a glass plate.

Since the microscope and inspection apparatus according to the invention aim to detect the defect existing inside of the semiconductor body, it is necessary to decrease the surface reflection occurred at the sample surface as much as possible. In order to decrease the surface reflection, according to the invention, the illumination beam is projected onto the sample surface at the incident angle which is substantially equal to the Brewster's angle of the sample. FIG. 4 is a graph showing a relation between the incident angle and the reflectivity of the silicon substrate. In FIG. 4, the abscissa denotes the incident angle and the vertical axis denotes the reflectivity of the silicon substrate. And, the broken line and solid line show properties of S-polarized light and p-polarized light, respectively. When the illumination light is P-polarized light and the incident angle is equal to the Brewster's angle of the silicon substrate, the reflectivity becomes zero and the illumination light can penetrate into the silicon substrate. The Brewster's angle of the silicon substrate is about 75°. Therefore, if the illumination beam is projected at the incident angle of 75°, the illumination optical system in which the surface reflection is zero is realized.

Furthermore, if the polarization maintaining fiber projects the illumination beam at the incident angle which is equal to the Brewster's angle, the illumination beam projecting section can be located in the space between the objective lens and the sample, the spatial limitation for the objective lens is reduced and thereby the objective lens having a large numerical aperture can be used. Particular, since the Brewster's angle of the silicon material is about 75° and the diameter of the tip portion of the polarization maintaining fiber is about 0.125 mm, it is possible to use an objective lens having a large numerical aperture and to carry out the defect inspection with high resolution.

Figure 5A:
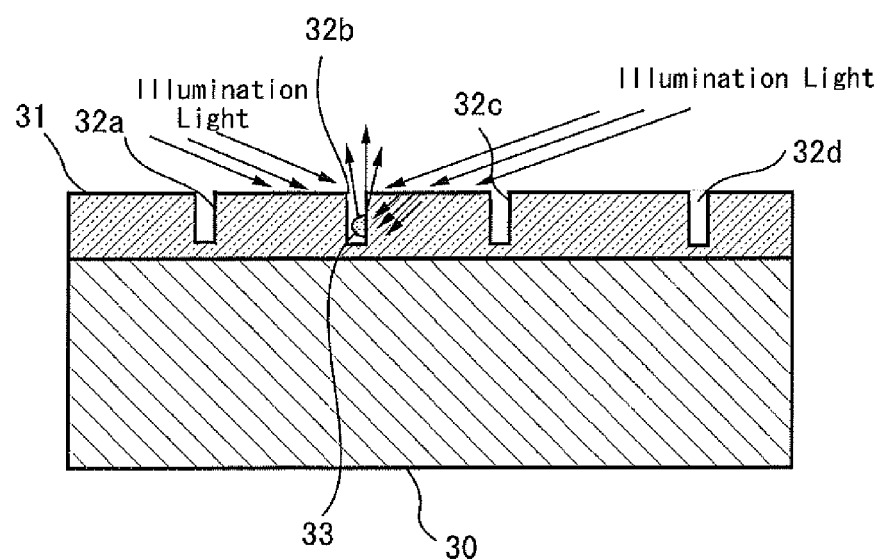
[FIGS. 5A and 5B] are views showing scattered light generation state.
Figure 5B:
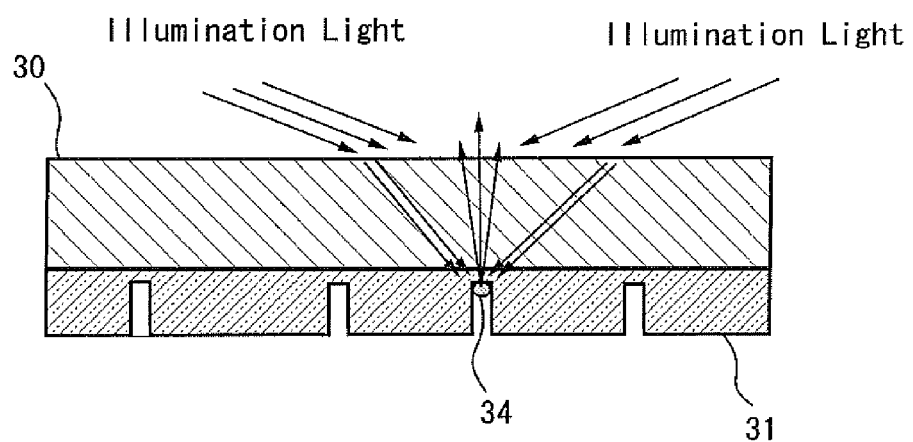

FIG. 5 shows the scattered light generation state. In the present example, as the sample to be inspected, a semiconductor body comprising a silicon substrate and a multilayered structure of various silicon material layers and silicon oxide layers is used. FIG. 5A shows an embodiment in which the illumination beam is projected from the top surface side at which the multilayered structure 31 is formed so as to detect the defect, and FIG. 5B shows an embodiment in which the illumination beam is projected from the rear surface side of the silicon substrate to detect the defect existing in the multilayered structure. Referring to FIG. 5A, the multilayered structure 31 is formed on the silicon substrate 30, and contact holes 32a~32d are formed in the multilayered structure 31. And, it is assumed that a column electrode is formed in the contact holes after the inspection is completed. It is assumed that the multilayered structure comprises single crystal or polycrystal silicon layers and silicon oxide layers which are formed alternatively. Now, it is assumed that the defect 33 formed by the foreign substance adhesion exists on the side wall of the contact hole 32b. If the illumination beam of P-polarized light having the center wavelength of the near infrared region is projected onto the surface of the multilayered structure 31 at the incident angle which is equal to the Brewster's angle, most of the illumination beam penetrates into the silicon material layer. In the normal area, the incident illumination light transmits through the multilayered structure 31 and the silicon substrate 30 and is emitted from the substrate. Contrary, when the illumination beam strikes on the side wall of the contact hole 32b, the illumination light is scattered by the defect 33 so that the scattered light is generated from the foreign substance 33. A part of the scattered light transmits through silicon material layers and is emitted from the multilayered structure, and is collected by the objective lens. Therefore, by detecting the scattered light collected by the objective lens using a photo-detector, the defect 33 can be detected. Further, since the reflection light reflected by the interface between the silicon substrate 30 and the multilayered structure 31 is emitted from the semiconductor body at the output angle of substantially 75° which deviates the collecting range of the objective, such reflection light is not captured by the objective lens.

As shown in FIG. 5B, according to the invention, it is possible to project the illumination beam from the rear surface side of the silicon substrate. That is, when the illumination beam of the P-polarized light having the center wavelength of the near infrared region is projected at the incident angle equal to the Brewster's angle from the rear surface side, no reflection occurs at the rear surface of the silicon substrate 30 and most of the illumination light penetrates into the substrate 30. The transmitted illumination light illuminates the multilayered structure 31 formed on the substrate 30 and the bottom surfaces and side walls of the contact holes 32a~32d. In this case, when the defect 34 formed by the foreign substance adhesion is present on the bottom surface of the contact hole 32c, the scattered light is generated by the defect present on the bottom surface. As this scattered light transmits through the multilayered structure 31 and the silicon substrate 30, such scattered light is emitted from the rear surface 30a of the silicon substrate 30 and is collected by the objective lens. Therefore, it is possible to detect the defect existing in the multilayered structure by projecting the illumination beam from the rear surface side of the silicon substrate.

This illumination method for projecting the illumination beam from the rear side of the silicon substrate is advantageous for the inspection which is performed in the manufacturing steps of the various devices such as a CMOS sensor. That is, in the manufacturing process of a CMOS sensor or a CCD sensor, the rear surface polishing step for polishing the rear surface of the silicon substrate is performed after the device forming area is formed on the top surface of the substrate. Therefore, the inspection method for projecting the illumination beam from the rear side of the substrate after the completion of the rear surface polishing is advantageous for the improvement of the yield rate.

In the present embodiment, the explanation was given of detection for the defect formed in the contact hole, but of course it is also possible to detect various defects existing in the silicon material layer.

Figure 6A:
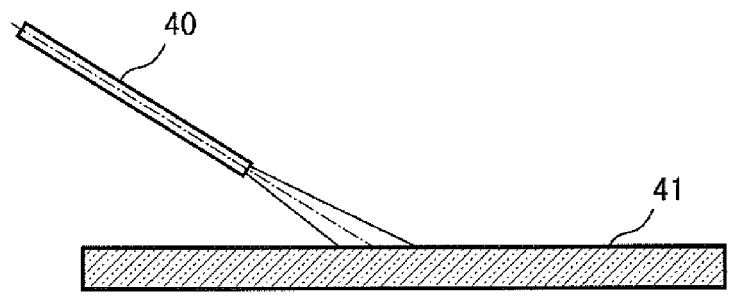
[FIGS. 6A~6D] are views showing the forms of the illumination beam exiting from the tip of the polarization maintaining fiber and the optical element fixed to the tip of the polarization maintaining fiber.

Next, prevention of the divergence of the illumination beam emanating from the polarization maintaining fiber will be explained. FIG. 6A shows the diverging state of the illumination beam emanating from the polarization maintaining fiber 40 and striking on the surface of the semiconductor body 41. As the illumination beam emanating from the polarization maintaining fiber is diverging beam, the illumination area which extends in the direction parallel with the incident plane and in the direction perpendicular to the incident plane is formed. Here, the incident plane means a plane which includes the optical axis of the illumination beam and is perpendicular to the sample surface. Since the illumination beam emanating from the polarization maintaining fiber is divergent, the marginal beam portion of the illumination beam is made incident on the sample surface at the incident angle deviated from the Brewster's angle, even if the polarization maintaining fiber is set at the Brewster's angle. As a result, it arises the problem that the intensity of the penetrating light of the marginal portion of the illumination area is decreased.

Figure 6B:
Figure 6C:
Figure 6D:
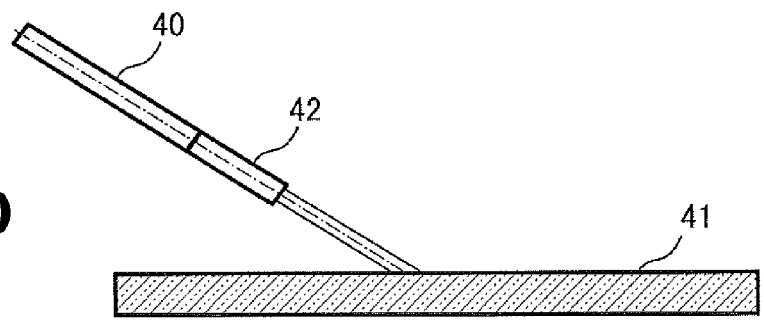

In order to overcome the above-mentioned problem, according to the invention, the tip of the polarization maintaining fiber 40 is provided with an optical element for controlling the divergence angle of the illumination beam. As shown in FIG. 6B, for instance a gradient index lens (GRIN lens) 42 can be used as the optical element. The gradient index lens is a lens element having a rod shape, and the diameter of the rod is substantially equal to that of the optical fiber. And also, the gradient index lens has the refractive index profile which becomes larger from the center toward the outside. In the present embodiment, the optical element 42 which functions a collimator lens is used as the gradient index lens. Such optical element can be fused to the tip of the polarization maintaining fiber by the arc discharge process. Therefore, as shown in FIG. 6D, if the optical element 42 which functions as the collimator lens is fixed to the tip of the polarization maintaining fiber, it is possible to project the illumination beam which is parallel to the optical axis of the illumination beam as a whole. As shown in FIG. 6C, it is also possible to use a rod-lens 43 in which the end surface 43a is formed as a spherical surface.

As the modification, it is possible to use a gradient index lens which functions as a cylindrical lens which converges only one direction so as to form the circular illumination area. When the polarization maintaining fiber (illumination beam projecting fiber) is set to the Brewster's angle, the illumination beam extends in the direction of the incident plane so that the shape of the illumination area is elliptical. In this case, if the cylindrical lens is used as the optical element which controls the divergence angle of the illumination beam, it is possible to form a substantially circular illumination area.

Figure 7A:
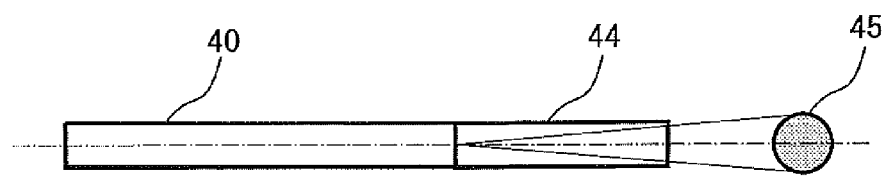
[FIGS. 7A and 7B] are views showing the forms of the illumination beam exiting from the cylindrical lens fixed to the tip of the polarization maintaining fiber.
Figure 7B:
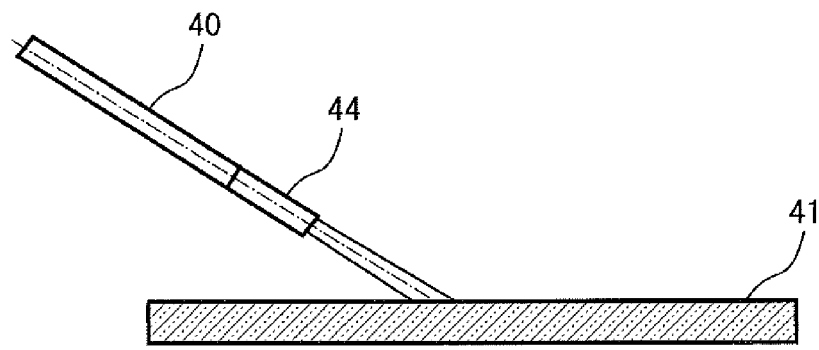

FIGS. 7A and 7B are a plan view and a side view showing the polarization maintaining fiber in which the cylindrical lens 44 is fused to the tip of the fiber 40. If the cylindrical rod-lens 44 is fused to the tip of the polarization maintaining fiber 40 and the convergence of the cylindrical lens is adjusted so that the divergence angle in the direction of the incident plane is smaller than the divergence angle of the polarization maintaining fiber, it is possible to form a substantially circular illumination area 45 on the sample surface.

FIG. 8 is a view showing one example of a signal processing unit. The image signal outputted from the TDI sensor 8 is amplified and then is supplied to the two-dimensional image forming means 50. The two-dimensional image forming means forms the two-dimensional image of the sample. In the present embodiment, the defect is detected by the die to die comparison checking. Therefore, the two-dimensional image forming means 50 forms the two-dimensional image of one die, and the formed image is supplied to the image memory 51. After the inspection of one die is completed, the inspection for the adjacent die is carried out. The image of the adjacent die is supplied from the two-dimensional image forming means 50 to the image memory 51 and to image comparison means 52. To the image comparison means 52, the last image stored in the image memory 51 is also supplied synchronously.

To the image comparison means 52, the image signals of the last die and the adjacent die in inspection are inputted in synchronization with each other. The image comparison means 52 compares the brightness of two inputted image signals with each other. If the difference in brightness beyond a given thresh-hold is detected, the image comparison means decides that the defect is present and supplies the defect signal to the defect memory 53. The output signal which is supplied from the position sensor 4 and represents the position of the stage is also supplied to the defect memory 53. Then, the defect memory 53 stores the address information received when the defect signal from the image comparison means 52 is inputted as the address information which represents the position of the defect. In this way, the address of the detected defect is stored in the defect memory.

Figure 9A:
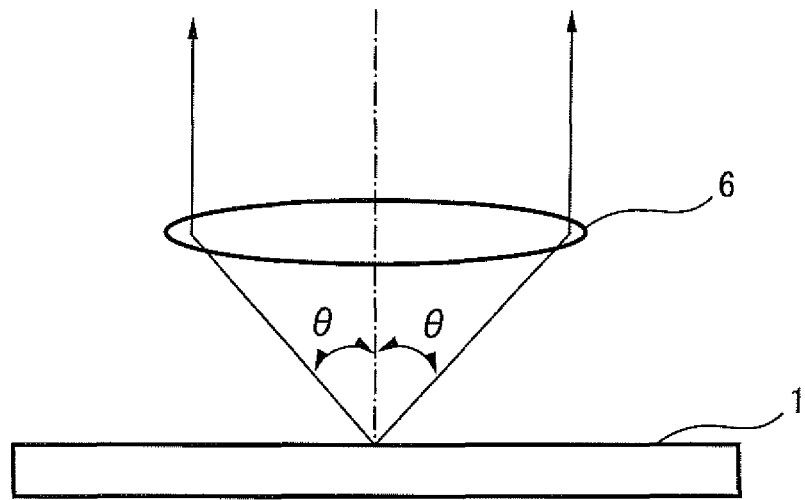
[FIGS. 9A and 9B] are views showing the range of the scattered light captured by the objective lens.
Figure 9B:
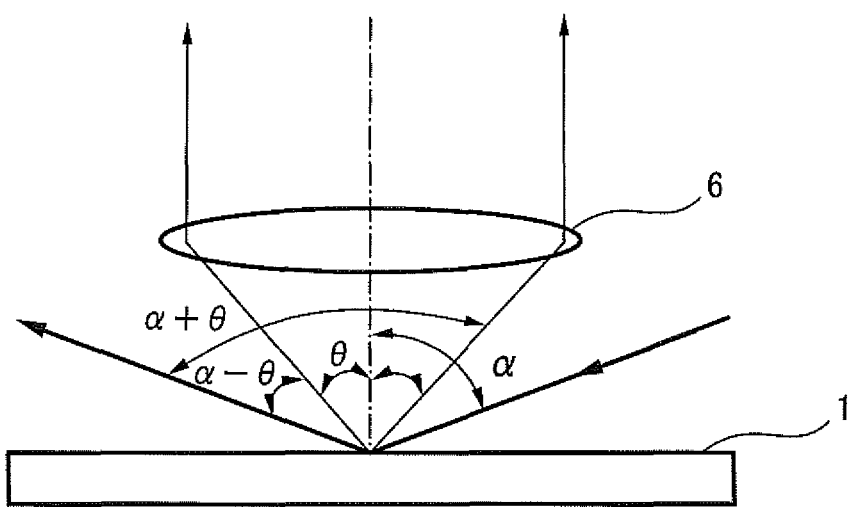

Next, the scattering angle of the scattered light which is collected by the objective lens will be explained. FIG. 9A denotes the collection range of the objective lens in the conventional reflection illumination system, and FIG. 9B denotes the collection range according to the invention. It is assumed that θ indicates the collection angle of the objective lens and α indicates the incident angle of the illumination beam according to the invention. In case of the reflection illumination, since the illumination beam is made incident on the sample surface perpendicularly, the range of the scattering angle collected by the objective lens is 0°~θ. On the contrary, in the illumination optical system of the invention, the range of the scattering angle collected by the objective lens is α−θ~α+θ. That is, in case of the reflection illumination, the scattered light having the relatively small scattering angle is collected by the objective lens, and the scattered light having the relative large scattering angle is not collected by the objective lens. Contrary, according to the invention, as the sample surface is illuminated by the off-axis illumination method, the scattered light having the relatively large scattering angle is collected by the objective lens and the scattered light having the small scattering angle is not collected.

Next, the relation between the size of the defect and the scattering angle will be discussed. In general, the scattering angle of the scattered light generated by the defect of large size is relative small, and the scattering angle of the scattered light generated by the defect of small size is relative large. Based on such technical recognition, in the microscope of the invention in which the sample surface is illuminated by the off-axis illumination method, the scattered light having large scattering angle is detected, and thus it becomes possible to detect the finer defect.

The present invention is not limited to the above-mentioned embodiments and can be modified and changed in various ways. For example, in the above-mentioned embodiment, four illumination beam projecting fibers are used to illuminate the sample surface from four directions, but it is possible to use a number of illumination projecting fibers. And also, it is possible that one polarization maintaining fiber is directly coupled to the light source apparatus so as to project one illumination beam of the P-polarized light from one direction. Furthermore, the central wavelengths are exemplified, and a plurality of SLEDs having different central wavelength each other can be used based on the optical characteristics of the sample.

In the above-mentioned embodiments, the explanation was given of the inspection apparatus in which the defect existing in the semiconductor body having the silicon substrate and the multilayered structure formed on the substrate is detected, but it is also possible to apply the present invention to the inspection apparatuses for inspecting various sample such as SiC substrate.

What is claimed is:

1. A microscope comprising a light source apparatus for producing linearly polarized light, a polarization maintaining fiber which is optically coupled to the light source apparatus to project the linearly polarized light emitted from the light source apparatus as an illumination beam of P-polarized light toward a sample surface, an objective lens which is arranged so that its optical axis is perpendicular to the sample surface so as to collect scattered light emitted from the sample, and a photo detector for receiving the scattered light collected by the objective lens, wherein said polarization maintaining fiber projects the illumination beam of the P-polarized light at an incidence angle which is substantially equal to the Brewster's angle of the sample.

2. The microscope of claim 1, wherein the tip of the polarization maintaining fiber is provided with an optical element which controls the divergence angle of the illumination beam.

3. The microscope of claim 2, wherein said optical element comprises a gradient index lens.

4. The microscope of claim 3, wherein said optical element functions as a collimator lens so as to project the parallel illumination beam of P polarized light.

5. The microscope of claim 2, wherein the light source apparatus comprises a super luminescent light emission diode which produces an incoherent light beam of the linearly polarized light.

6. The microscope of claim 2, wherein the light source apparatus comprises a plurality of super luminescent light emission diodes which produce the incoherent light beams of the linearly polarized light, and wherein the polarization maintaining fiber is coupled to the super luminescent light emission diodes through one or a plurality of optical fiber couplers.

7. The microscope of claim 6, wherein the plural super luminescent light emission diodes produce the light beams of the linearly polarized light having the same wavelength.

8. The microscope of claim 6, wherein the plural super luminescent light emission diodes produce the light beams of the linearly polarized light having different wavelengths each other.

9. The microscope of claim 1, wherein the sample is a semiconductor body comprising a silicon substrate and one or a plurality of semiconductor layers formed on the silicon substrate, and wherein the light source apparatus produces the illumination beam of infrared light which is transparent to the silicon material.

10. A microscope comprising a light source apparatus for producing linearly polarized light, a plurality of polarization maintaining fibers which are optically coupled to the light source apparatus to project the linearly polarized light emitted from the light source apparatus as illumination beams of P-polarized light toward a sample surface, an objective lens which is arranged so that its optical axis is perpendicular to the sample surface so as to collect scattered light emitted from the sample, and a photo detector for receiving the scattered light collected by the objective lens, wherein
the polarization maintaining fibers project the illumination beams of the P polarized light at an incidence angle which is substantially equal to the Brewster's angle of the sample.

11. The microscope of claim 10, wherein each tip of the polarization maintaining fibers are provided with a gradient index lens for controlling the divergence angle of the illumination beam.

12. The microscope of claim 11, wherein the gradient index lens functions as a collimator lens so as to project the parallel illumination beam of P polarized light.

13. The microscope of claim 11, wherein the light emitting ends of the plural polarization maintaining fibers are circularly arranged around the illumination area, and wherein the illumination area of the sample surface is illuminated from different angular directions.

14. The microscope of claim 11, wherein the light source apparatus includes one or a plurality of super luminescent light emission diodes which produce incoherent light beams of linearly polarized light.

15. The microscope of claim 11, wherein the light source apparatus includes a plurality of super luminescent light emission diodes which produce the incoherent light beams of the linearly polarized light having the same wavelength or different wavelengths each other, and wherein the plural polarization maintaining fibers are connected to the plural super luminescent light emission diodes through optical fiber couplers.

16. The microscope of claim 15, wherein the optical fiber couplers comprises a WDM coupler and a 3 dB coupler.

17. The microscope of claim 10, wherein the sample is a semiconductor body comprising a silicon substrate and one or a plurality of semiconductor layers formed on the silicon substrate, and wherein the light source apparatus produces the light beam of infrared light which is transparent to the silicon material.

18. The microscope of claim 15, wherein the objective lens collects the scattered light generated in the semiconductor layers or the scattered light generated by a hole or a groove formed in the semiconductor layer.

19. An inspection apparatus for detecting a defect existing in a sample, the inspection apparatus comprising;
a stage arranged to move along a first direction and a second direction perpendicular to the first direction and to hold a sample to be inspected,
a light source apparatus for producing linearly polarized light,
a polarization maintaining fiber which is optically coupled to the light source apparatus to project the linearly polarized light emitted from the light source apparatus as an illumination beam of P-polarized light toward a sample surface,
an objective lens which is arranged so that its optical axis is perpendicular to the sample surface so as to collect scattered light emitted from the sample,
a photo detector for receiving the scattered light collected by the objective lens, and
a signal processing unit coupled to the photo detector and processing the output signals supplied from the photo detector to produce data indicative of the defect, wherein
said polarization maintaining fiber projects the illumination beam of the P polarized light at an incidence angle which is substantially equal to the Brewster's angle of the sample.

20. The inspection apparatus of claim 19, wherein the tip of the polarization maintaining fiber is provided with an optical element for controlling the divergence angle of the illumination beam.

21. The inspection apparatus of claim 20, wherein the optical element comprises a gradient index lens which functions as a collimator lens so as to project the parallel illumination beam of P polarized light.

22. The inspection apparatus of claim 20, wherein the light source apparatus includes one or a plurality of super luminescent light emission diodes which produce incoherent light beams of the linearly polarized light.

23. The inspection apparatus of claim 22, wherein the light source apparatus includes a plurality of super luminescent light emission diodes which produce the coherent light beams of the linearly polarized light having the same wavelength or different wavelengths each other.

24. The inspection apparatus of claim 22, wherein the super luminescent light emission diodes produce the coherent light beams of the linearly polarized light having the different wavelengths each other, and wherein the illumination area of the sample surface is illuminated by the illumination beams having different wavelengths each other by selectively turning on the super luminescent light emission diodes.

25. The inspection apparatus of claim 22, wherein the plural illumination beams having different wavelengths each other are simultaneously projected toward the illumination area, and wherein the sample surface to be inspected is simultaneously scanned by the plural illumination beams having different wavelengths.

26. The inspection apparatus of claim 19, wherein the sample is a semiconductor body comprising a silicon substrate and a multilayer structure including a plurality of semiconductor layers formed on the silicon substrate, and wherein the light source apparatus produces the linearly polarized light of infrared light which is transparent to the silicon substrate.

27. The inspection apparatus of claim 26, wherein the multilayer structure including a silicon oxide layer and a semiconductor layer.

28. The inspection apparatus of claim 26, the illumination beam is projected onto the rear surface of the silicon substrate in which the multilayer structure is not formed.

29. The inspection apparatus of claim 28, wherein the objective lens collects the scattered light which is generated in the multilayer structure and transmits through the silicon substrate.

30. The inspection apparatus of claim 19, wherein during inspection, the stage moves along the first direction and second direction in zigzag fashion so that the surface of the sample is scanned by the illumination beam.

31. The inspection apparatus of claim 30, wherein the photo detector comprises an imaging sensor.

32. An inspection apparatus for detecting a defect existing in a sample, the inspection apparatus comprising;
   a stage arranged to move along a first direction and a second direction perpendicular to the first direction and to hold a sample to be inspected,
   a light source apparatus for producing linearly polarized light,
   a plurality of polarization maintaining fibers which are optically coupled to the light source apparatus to project the linearly polarized light emitted from the light source apparatus as an illumination beams of P-polarized light toward a sample surface,
   an objective lens which is arranged so that its optical axis is perpendicular to the sample surface so as to collect scattered light emitted from the sample,
   a photo detector for receiving the scattered light collected by the objective lens, and
   a signal processing unit coupled to the photo detector and processing the output signals supplied from the photo detector to produce data indicative of the defect, wherein
   said plural polarization maintaining fibers project the illumination beams of the P polarized light at an incidence angle which is substantially equal to the Brewster's angle of the sample.

33. The inspection apparatus of claim 32, wherein the tips of the polarization maintaining fibers are provided with an optical element for controlling the divergence angle of the illumination beam.

34. The inspection apparatus of claim 33, wherein the optical element functions as a collimator lens so as to project the parallel illumination beam of P polarized light.

35. The inspection apparatus of claim 33, wherein the light emitting ends of the plural polarization maintaining fibers are circularly arranged around the illumination area and the illumination area of the sample surface is illuminated from different angular directions.

36. The inspection apparatus of claim 33, wherein the sample is a semiconductor body comprising a silicon substrate and a multilayered structure formed on the silicon substrate, and wherein the light source apparatus produces the light beam of infrared light which is transparent to the silicon material.

37. The inspection apparatus of claim 36, wherein the illumination beam is projected toward the rear surface of the silicon substrate in which the multilayered structure is not formed.

* * * * *